(12) United States Patent
Nguyen

(10) Patent No.: US 10,231,948 B2
(45) Date of Patent: Mar. 19, 2019

(54) METERED DOSE INHALER COMPOSITIONS, SYSTEMS, AND METHODS

(71) Applicant: Jason Ty Nguyen, Phoenix, AZ (US)

(72) Inventor: Jason Ty Nguyen, Phoenix, AZ (US)

(*) Notice: Subject to any disclaimer, the term of this patent is extended or adjusted under 35 U.S.C. 154(b) by 0 days.

(21) Appl. No.: 15/905,662

(22) Filed: Feb. 26, 2018

(65) Prior Publication Data

US 2018/0243259 A1    Aug. 30, 2018

Related U.S. Application Data

(60) Provisional application No. 62/463,925, filed on Feb. 27, 2017.

(51) Int. Cl.

| A61K 36/00 | (2006.01) |
|---|---|
| A61K 31/352 | (2006.01) |
| A61K 9/00 | (2006.01) |
| A61K 47/10 | (2017.01) |
| A61K 9/12 | (2006.01) |
| A61K 36/185 | (2006.01) |
| A61M 15/00 | (2006.01) |
| A61K 47/06 | (2006.01) |
| A61K 47/14 | (2017.01) |

(52) U.S. Cl.
CPC ............ *A61K 31/352* (2013.01); *A61K 9/008* (2013.01); *A61K 9/124* (2013.01); *A61K 36/185* (2013.01); *A61K 47/06* (2013.01); *A61K 47/10* (2013.01); *A61K 47/14* (2013.01); *A61M 15/009* (2013.01); *A61M 2205/12* (2013.01)

(58) Field of Classification Search
CPC ...................................... A61K 36/00
USPC ........................................ 424/725
See application file for complete search history.

(56) References Cited

U.S. PATENT DOCUMENTS

| 6,149,892 A | 11/2000 | Britto |
|---|---|---|
| 6,509,005 B1 | 1/2003 | Peart et al. |
| 6,713,048 B2 | 3/2004 | Peart et al. |
| 7,223,381 B2 | 5/2007 | Lewis et al. |
| 7,347,199 B1 | 3/2008 | Lewis et al. |
| 8,142,763 B2 | 3/2012 | Lewis et al. |
| 2004/0223916 A1 | 11/2004 | Burt et al. |
| 2005/0042172 A1 | 2/2005 | Whittle |
| 2005/0079136 A1 | 4/2005 | Woolfe et al. |
| 2007/0104741 A1 | 5/2007 | Murty et al. |
| 2007/0286814 A1 | 12/2007 | Sawant et al. |
| 2008/0017191 A1 | 1/2008 | Davies et al. |
| 2010/0196488 A1 | 8/2010 | Whittle |
| 2010/0273895 A1 | 10/2010 | Stinchcomb et al. |
| 2015/0231108 A1 | 8/2015 | Hearn et al. |

FOREIGN PATENT DOCUMENTS

| WO | WO2003097141 A2 * | 11/2003 |
|---|---|---|
| WO | WO2015200049 a1 | 12/2015 |

OTHER PUBLICATIONS

D. Gold, Advanced Refinement Techniques, publication date unknown but at least as early as Dec. 27, 2015. http://www.kindgreenbuds.com/cannabis-alchemy/advanced-refinernent-techniques/.

Bianca Fox, Unveiling the Future: The Process and Applications of Cannabinoid Distillates, Jun. 26, 2016. http://www.dopemagazine.com/unveiling-future-cannabinoid-distillates/.

* cited by examiner

*Primary Examiner* — Michael V Meller
(74) *Attorney, Agent, or Firm* — Scott A. Hill; The Hill Law Firm, PLC

(57) ABSTRACT

Compositions, systems, and methods that can be used with a pressurized metered dose inhaler are disclosed. A pharmaceutical composition for use in a pressurized metered dose inhaler can comprise a cannabinoid composition, a co-solvent, a terpene composition, and a propellant. A pharmaceutical composition may be soluble. A system can comprise a plurality of cannabinoid compositions and/or a plurality of terpene compositions available in various combinations. One of a plurality of cannabinoid compositions and terpene composition combinations may be user-selectable in response to various factors such as a desired therapeutic benefit, sedative effect, flavor profile, or a combination of the foregoing. A method of formulating a soluble pMDI pharmaceutical composition comprising a cannabinoid composition, a co-solvent, a terpene composition, and a propellant is disclosed.

1 Claim, No Drawings

METERED DOSE INHALER COMPOSITIONS, SYSTEMS, AND METHODS

CROSS-REFERENCE TO RELATED APPLICATIONS

This application is a non-provisional of prior application Ser. No. 62/463,925, filed Feb. 27, 2017, incorporated herein.

FIELD

The present disclosure relates to compositions, systems, and methods for metered dose inhalers. In particular, the disclosure relates to metered dose inhaler formulations and systems comprising cannabinoids and terpenoids and methods for producing the same.

BACKGROUND

The rapid expansion of legal markets for medical and adult *cannabis* products in the United States and other countries has spurred an increase in the number and variety of *cannabis*-containing products along with a widening variety of consumption or delivery methods in recent years. Use of smoking or vaping apparatus to deliver aerosolized cannabinoid bioactive compounds in inhaled smoke or vapor remains a popular consumption method, since the inhaled cannabinoid compounds are readily absorbed in pulmonary tissues. Inhalation provides a more rapid onset of pharmacological action and peak plasma levels than ingestion, although various types of edible or orally consumed products have become popular as well. The pharmacokinetics achieved via pulmonary delivery are comparable to those achieved via intravenous administration, but inhalation is a much less invasive approach that is also more convenient for self-medication.

For many consumers or patients using *cannabis* products as a medicine, traditional inhalation-based delivery methods involving combustion may be undesirable due to various potential risks or negative side-effects of smoking. In addition, smoking can be inconvenient and can pose challenges to consistent dosing and discrete administration. Various methods of inhalation delivery using electronic vaporizers partially address some of the negative aspects of combustion-based smoking. However, plant matter, concentrate, and liquid product vaporizers are subject to various other inconveniences, including cleaning, maintenance, charging, etc. Other inhalation delivery systems such as metered dose inhalers have been described that address certain shortcomings of inhalation-based delivery methods relying on combustion or vaporization; however, such products have been narrowly THC-focused, perform poorly due to clogging or other issues, or are devoid of other aspects associated with *cannabis* consumption, such as providing the consumer or patient with an ability to select various cannabinoid profiles and/or other product attributes that affect a consumer's experience. Therefore, improved metered dose inhaler formulations and systems are desirable.

SUMMARY OF THE INVENTION

The present invention is for improved compositions, systems, and methods that can be used with a pressurized metered dose inhaler. A pharmaceutical composition for use in a pressurized metered dose inhaler can comprise a cannabinoid composition, a co-solvent, a terpene composition, and a propellant. A pharmaceutical composition may be soluble. An inhaler system with actuator can comprise a plurality of cannabinoid compositions and/or a plurality of terpene compositions available in various interchangeable canister assembly combinations. One of a plurality of cannabinoid compositions and terpene composition combinations may be user-selectable in response to various factors such as a desired therapeutic benefit, sedative effect, flavor profile, or a combination of the foregoing. A method of formulating a soluble pMDI pharmaceutical composition, for use with the inhaler system, comprising a cannabinoid composition, a co-solvent, a terpene composition, and a propellant is disclosed.

DETAILED DESCRIPTION

The detailed description of herein makes reference to exemplary embodiments by way of illustration and their best mode. While these exemplary embodiments are described in sufficient detail to enable those skilled in the art to practice the inventions, it should be understood that other embodiments may be realized and that logical and mechanical changes may be made without departing from the spirit and scope of the inventions. Thus, the detailed description herein is presented for purposes of illustration only and not by way of limitation. For example, the steps recited in any method or process descriptions herein may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

As used herein, the term "cannabinoid composition" means any composition of matter comprising one or more cannabinoid compounds. A cannabinoid composition can include a single isolated cannabinoid compound or a mixture of cannabinoids, whether in purified form or in a solution or other physical or chemical matrix As used here, the terms "cannabinoid" and "cannabinoid compound" may be used interchangeably and mean any chemical molecule capable of interacting with or acting on a mammalian cannabinoid receptor, such as human cannabinoid receptor type 1 ($CB_1$) or cannabinoid receptor type 2 ($CB_2$). This can include endocannabinoids produced endogenously by humans and other mammals, phytocannabinoids occurring in various plant species, and synthetic cannabinoids, whether or not derived from *cannabis* plants.

As used herein, the term "*cannabis*" means any plant or plant material of the genus *Cannabis*, including without limitation plants identified as *Cannabis sativa, Cannabis indica,* and *Cannabis ruderalis,* along with various other species, subspecies, hybrids, strains, chemovars, and other genetic variants of the same.

As used herein, the term "*cannabis* extract" means an extract derived from *cannabis* plant material by any process suitable to separate cannabinoid compounds and/or terpene compounds from the plant material. A *cannabis* extract can be produced, for example, by solvent extraction using various solvents, whether at supercritical or subcritical pressures. In various embodiments, a *cannabis* extract may be subject to further processing to remove non-target constituents that may be co-extracted with cannabinoid and/or terpenoid compounds, such as chlorophyll, waxes, and other materials. In various embodiments, a *cannabis* extract can comprise substantially all of the cannabinoids present in the plant in substantially the same relative abundance and form (including the cannabinoid acid form) in which they occur in the plant tissue from which they were extracted.

As used herein, the term "cannabinoid molecular distillate" means a composition of cannabinoid compounds purified or isolated from a *cannabis* extract by a short path distillation process. A "cannabinoid molecular distillate" can comprise one or more distinct cannabinoid compounds. A short path distillation process includes any distillation performed under conditions such that a vapor molecule escaping a warmed input fluid is unlikely to encounter another vapor molecule (i.e., undergo an intermolecular collision) prior to reaching a cooled condenser surface. Suitable short path distillation apparatus for producing a molecular distillate include, for example, a thin film distillation apparatus, a wiped film distillation apparatus, a Kugelrohr short path distillation apparatus, and the like.

In various embodiments, a cannabinoid molecular distillate may be characterized according to the source of the material used to produce the *cannabis* extract subject to distillation. For example, the term "marijuana flower cannabinoid molecular distillate" can be used to describe a collection of cannabinoid compounds purified or isolated from a *cannabis* extract produced from marijuana flower material. The term "hemp cannabinoid molecular distillate" can be used to describe a collection of cannabinoid compounds purified or isolated from a *cannabis* extract produced from plant material that would be legally or technically classified as "hemp," such as a variety of *Cannabis sativa* having a THC content of less than 0.3% by dry weight.

As used herein, the terms "terpene" and "terpenoid compound" may be used interchangeably and mean any chemical molecule, whether natural or synthetic, derived from one or more isoprene chemical subunits, except that various terpenophenolic compounds meeting the definition of "cannabinoid" provided above are not included within the meaning of the terms "terpene" or "terpenoid compound."

As used herein, the term "therapeutic substance" means any compound or agent which may be administered to a human or animal subject for the purpose of providing some therapeutic benefit to the subject. "Therapeutic benefit" in this context includes prophylactic treatment for the purposes of preventing a physical or medical condition, as well as treatment aimed at alleviating the symptoms of a physical or medical condition. Suitable "therapeutic substances" include conventional pharmacologically active pharmaceutical substances and medicaments as well as compounds or compositions derived from plants that may provide therapeutic effects.

As used herein, the term "therapeutically effective amount" or "therapeutically and/or prophylactically effective amount" means an amount of compound or agent sufficient to elicit the required or desired therapeutic and/or prophylactic response, as the particular treatment context may require. It will be understood that a therapeutically and/or prophylactically effective amount of a drug for a subject may be dependent on variables such as the body weight of the subject as well as other factors known to a person of ordinary skill in the art.

As used herein, the term "treating" means to alleviate symptoms, eliminate the causation of the symptoms either on a temporary or permanent basis, or to slow the appearance of symptoms of a disorder or condition.

Pharmaceutical Compositions

In accordance with various embodiments of the present disclosure, a pharmaceutical composition can comprise a cannabinoid composition, a terpene composition, a co-solvent, and a propellant. A pharmaceutical composition can be configured for pulmonary administration, such as via a pressurized metered dose inhaler (pMDI). A pharmaceutical composition in accordance with various embodiments can be configured to provide for stability of the pharmaceutical composition, including, for example, physical and chemical stability of the pharmaceutical composition during manufacturing, storage, handling, and use of a pMDI system comprising the pharmaceutical composition. In various embodiments, a pharmaceutical composition can be formulated to provide for solubility of the cannabinoid composition and the individual cannabinoid components thereof and/or the terpene composition and the individual terpenoid components thereof in a liquid solution comprising the cannabinoid composition, the co-solvent, the terpene composition, and the propellant in a pressurized metered dose inhaler canister assembly, as described in greater detail below.

In accordance with various embodiments, a cannabinoid composition, a terpene composition, a co-solvent, and a propellant may be combined in relative quantities that provide for a stable solution. For example, in various embodiments, a pharmaceutical composition can be configured such that the cannabinoid composition comprises about 14% to about 20% by weight (w/w) of the composition, the co-solvent comprises about 14% to about 20% by weight (w/w) of the composition, the terpene composition comprises about 0.5% to about 4.0% by weight (w/w) of the composition, and the propellant comprises about 55% to about 72% (w/w) of the composition. Various pharmaceutical compositions in accordance with various embodiments of the present disclosure are described in greater detail below.

A pharmaceutical composition in accordance with various embodiments can comprise one or more therapeutic substances. In various embodiments, a therapeutic substance can comprise a cannabinoid composition and/or a terpenoid composition. In various embodiments and as described in greater detail below, a system of pharmaceutical compositions comprising different combinations of cannabinoid compositions and terpene compositions is provided. A system of pharmaceutical compositions in accordance with various embodiments may enable patients to select from among various permutations of therapeutic substances and flavor profiles and administer a selected pharmaceutical composition in response to one or more of a desired therapeutic benefit, a desired sedation level, and a desired flavor profile.

Cannabinoid Compositions

In accordance with various embodiments, a cannabinoid composition can comprise a single cannabinoid compound or a plurality of cannabinoid compounds. A cannabinoid composition comprising a single cannabinoid compound can include, for example a cannabinoid compound that is isolated or purified from a natural source such as a *cannabis* plant, or a chemically-synthesized cannabinoid compound.

In various embodiments, a cannabinoid composition can include, but is not limited to, cannabinoid compounds that may naturally occur in different combinations and relative quantities in the plant tissues of various species, subspecies, hybrids, strains, chemovars, and other genetic variants of the genus *Cannabis*, including in material that may variously be classified as "marijuana" and "hemp" in accordance with various legal or technical definitions and standards. These cannabinoid compounds can include, for example, delta-9-tetrahydrocannabinol (THC), tetrahydrocannabinolic acid (THCA), delta-8-tetrahydrocannabinol (D8THC), cannabidiol (CBD), cannabidiolic acid (CBDA), cannabinol (CBN), cannabinolic acid (CBNA), tetrahydrocannabinovarin (THCV), tetrahydrocannabinovarinic acid (THCVA), cannabidivarin (CBDV), cannabidivarin acid (CBDVA), cannabigerol (CBG), cannabigerolic acid (CBGA), cannabichromene (CBC), cannabichromenic acid (CBCA), cannabinodiol (CBND), and cannabinodiolic acid (CBNDA). In various embodiments, a cannabinoid composition can include naturally-occurring cannabinoid compounds that are produced via synthetic chemistry means, synthetic analogs and derivatives of naturally-occurring cannabinoids, and various combinations of natural and synthetic cannabinoids.

In various embodiments, a cannabinoid composition can comprise a plurality of cannabinoid compounds. A cannabinoid composition can comprise a plurality of cannabinoid compounds extracted, isolated, or purified from a *cannabis* plant. For example, in various embodiments, a cannabinoid composition can comprise a cannabinoid molecular distillate comprising a plurality of cannabinoid compounds. In various embodiments, a cannabinoid molecular distillate can comprise at least about 80% cannabinoid compounds by weight, or at least about 85% cannabinoid compounds by weight, or at least about 90% cannabinoid compounds by weight, or at least about 95% cannabinoid compounds by weight, or at least about 96% cannabinoid compounds by weight, or at least about 97% cannabinoid compounds by weight, or at least about 98% cannabinoid compounds by weight, or at least about 99% cannabinoid compounds by weight.

In various embodiments, a cannabinoid composition can comprise a *Cannabis sativa* cannabinoid composition, a *Cannabis indica* cannabinoid composition, or a hybrid cannabinoid composition, derived from extracts of *Cannabis sativa, Cannabis indica*, and hybrid *cannabis* plants, respectively. As used herein, "derived from" can mean extracted, isolated, or purified from a *cannabis* plant, as well as mixed or synthesized to simulate a cannabinoid composition obtained from a *cannabis* plant. For example, in various embodiments, a cannabinoid composition can comprise a *Cannabis indica* molecular distillate produced from an extract obtained from *Cannabis indica* plant material.

In various embodiments, a cannabinoid composition comprising a plurality of cannabinoid compounds can comprise at least two, or at least three, or at least four cannabinoid compounds. In various embodiments, a cannabinoid composition can comprise a plurality of cannabinoid compounds selected from the group consisting of THC, THCA, D8THC, CBD, CBDA, CBN, CBNA, THCV, THCVA, CBDV, CBDVA, CBG, CBGA, CBC, CBCA, CBND, and CBNDA. In various embodiments, a cannabinoid composition can comprise a plurality of cannabinoid compounds selected from the group consisting of THC, CBC, CBN, CBG, and THCV.

In various embodiments, a cannabinoid composition comprising a plurality of cannabinoid compounds can comprise THCV. The THCV can comprise at least about 0.5% of the cannabinoid composition by weight.

In various embodiments, a cannabinoid composition comprising a plurality of cannabinoid compounds can comprise CBG, CBN, and CBC. In various embodiments, CBG can comprise at least about 1.0% of the cannabinoid composition by weight, and the CBN can comprise at least about 2.0% of the cannabinoid composition by weight.

Specific combinations of various cannabinoids have been found to be clinically useful in the treatment or management of specific diseases or medical conditions. In various embodiments, a cannabinoid composition can comprise specific ratios of certain cannabinoids, such as a specific ratio of CBD to THC. For example, in various embodiments, a cannabinoid composition can comprise about a 0:1, or a about a 1:0, or about a 1:1, or about a 2:1, or about a 3:1, or about a 4:1, or about a 5:1, or about a 6:1, or about a 7:1, or about a 8:1, or about a 9:1, or about a 10:1, or about a 15:1, or about a 20:1, or about a 25:1 ratio of CBD to THC by weight or relative abundance (i.e., molar concentration). Likewise, a cannabinoid composition can comprise any two cannabinoid compounds in the foregoing ratios or similar approximations thereof. In various embodiments, the ratio between any two cannabinoids in a cannabinoid composition can be any ratio between, for example, about 0:1 and about 100:1.

In various embodiments, a cannabinoid composition may be substantially devoid of CBD. As used herein, the term "substantially devoid" means having an undetectable amount of a substance, or less than about 0.1% of a composition by weight. In various embodiments, a pharmaceutical composition can comprise a cannabinoid composition that contains less than about 0.1% CBD by weight of the cannabinoid composition.

In various embodiments, a cannabinoid composition can comprise CBD. The CBD can be derived from a *cannabis* or hemp extract and can be a *cannabis* or hemp extract molecular distillate that may comprise further cannabinoid compounds, or the CBD can be derived from a CBD isolate, whether synthesized or obtained by purification from a *cannabis* or hemp source. In various embodiments, a cannabinoid composition comprising CBD can comprise a plurality of cannabinoids, such as various cannabinoids selected from the group consisting of THC, THCA, D8THC, CBDA, CBN, CBNA, THCV, THCVA, CBDV, CBDVA, CBG, CBGA, CBC, CBCA, CBND, and CBNDA.

In various embodiments and as mentioned above, a cannabinoid composition can comprise both decarboxylated cannabinoid compounds as well as the corresponding carboxylic acid forms, such as, for example, both THC and THCA. A *cannabis* extract or cannabinoid composition can be decarboxylated, such as by heating, and in various embodiments, a cannabinoid composition can be substantially devoid of acid forms of cannabinoid compounds. However, a *cannabis* extract or cannabinoid composition need not be decarboxylated, and a cannabinoid composition may comprise one or more carboxylic acid cannabinoid forms. In various embodiments, the carboxylic acid forms of one or more cannabinoid compounds in a cannabinoid composition may be present in a higher abundance than the corresponding decarboxylated form.

In various embodiments, a pharmaceutical composition can comprise a cannabinoid composition formulated to provide a particular therapeutic benefit. Such a composition can be configured to provide a pharmacologically effective amount and/or a therapeutically effective amount of one or more specific cannabinoid compounds. For example, in various embodiments, a pharmaceutical composition can be formulated with a cannabinoid composition comprising a pharmacologically effective amount and/or a therapeutically effective amount of at least one of the cannabinoid compounds selected from the group consisting of CBD, CBC, and CBN to provide a sedative or anti-insomnia therapeutic benefit.

In various embodiments, a pharmaceutical composition comprising a cannabinoid composition configured to provide a particular therapeutic benefit can further comprise a synergistic terpene composition configured to provide an enhanced therapeutic benefit. For example, and as described in greater detail below, a pharmaceutical composition comprising a cannabinoid composition configured to provide a sedative or anti-insomnia therapeutic benefit can further comprise a terpene composition comprising, for example, a pharmacologically effective amount and/or a therapeutically effective amount of a terpene selected from the group consisting of β-myrcene, linalool, d-limonene, nerolidol, and terpinolene. In various embodiments, a pharmaceutical composition configured to provide a sedative therapeutic benefit can comprise a terpene composition including at least 20% by weight of terpenoid compounds selected from the group consisting of β-myrcene, linalool, and d-limonene. In various embodiments, a pharmaceutical composition configured to provide a sedative therapeutic benefit can comprise a terpene composition including one of sabinene and α-phellandrene.

In various embodiments of a pharmaceutical composition comprising a cannabinoid composition such as a cannabinoid molecular distillate, the cannabinoid composition can comprise from about 1% to about 30%, or from about 10% to about 25%, or from about 12% to about 22%, or from about 14% to about 19% by weight (w/w) of the pharmaceutical composition. In various embodiments, a cannabinoid composition can comprise at least about 5%, or at least about 10%, or at least about 12%, or at least about 14%, or at least about 15%, or at least about 16%, or at least about 17%, or at least about 18%, or at least about 19%, or at least about 20%, or at least about 21%, or at least about 22%, or at least about 23%, or at least about 24%, or at least about 25% by weight (w/w) of a pharmaceutical composition.

In various embodiments, a pharmaceutical composition comprising a cannabinoid composition can be configured to deliver a particular amount of the cannabinoid composition with each actuation of a pMDI system containing the pharmaceutical composition. For example, in various embodiments, a pharmaceutical composition can be formulated to deliver about 1 mg, or about 2 mg, or about 3 mg, or about 4 mg, or about 5 mg, or about 10 mg, or about 15 mg, or about 20 mg, or about 25 mg, or about 50 mg of a cannabinoid composition per actuation. In various embodiments and as mentioned above, a pharmaceutical composition can be formulated to deliver a pharmacologically effective amount and/or a therapeutically effective amount of one or more specific cannabinoid compounds, as described in greater detail below.

Terpene Compositions

In various embodiments of the present disclosure, a pharmaceutical composition can comprise a terpene composition. However, a pharmaceutical composition in accordance with various embodiments need not comprise a terpene composition, and in various embodiment, a pharmaceutical composition can be substantially free of terpenoid compounds.

In accordance with various embodiments, a pharmaceutical composition can comprise, for example, from about 0.2% to about 2% by weight (w/w) of a terpene composition. In various embodiments, a pharmaceutical composition can comprise at least about 0.1%, or at least about 0.2%, or at least about 0.5%, or at least about 0.75%, or at least about 1.0%, or at least about 1.25%, or at least about 1.5%, or at least about 1.75%, or at least about 2.0%, or at least about 3.0%, or at least about 4.0%, or at least about 5.0%, or at least about 6.0%, or at least about 7.0%, or at least about 8.0%, or at least about 9.0%, or at least about 10%, or at least about 11%, or at least about 12%, or at least about 13%, or at least about 14%, or at least about 15%, or at least about 16%, or at least about 17%, or at least about 18%, or at least about 19%, or at least about 20% by weight (w/w) of a terpene composition.

In accordance with various embodiments, a terpene composition can comprise a single terpenoid compound or a plurality of terpenoid compounds. A terpene composition comprising a single cannabinoid compound can include, for example a terpene compound that is isolated or purified from a natural source such as a *cannabis* plant, or a chemically-synthesized terpenoid compound.

In various embodiments, a terpene composition comprising a plurality of terpenoid compounds can comprise at least two, or at least three, or at least four terpenoid compounds. In various embodiments, a terpene composition can comprise a plurality of terpenoid compounds selected from the group consisting of α-pinene, camphene, α-pinene, β-pinene, β-myrcene, δ-3-carene, d-limonene, α-terpinene, p-cymene, eucalyptol, ocimene, γ-terpinene, terpinolene, linalool, (−)-isopulegol, geraniol, β-caryophyllene, α-humulene, nerolidol, (−)-guaiol, (−)-α-bisabolol, (−)-caryophyllene oxide, α-phellandrene, fenchol, borneol, terpineol, sabinene, camphor, isoborneol, α-cedrene, phytol, valencene, pulegone geranyl acetate, and menthol.

In various embodiments, a terpene composition can comprise a plurality of terpene compounds extracted, isolated, or purified from a *cannabis* plant or another plant species. For example, in various embodiments, a terpene composition can comprise a terpene distillate comprising a plurality of terpene compounds. In various embodiments, a terpene distillate can be obtained from a marijuana flower extract or from a hemp extract. In various embodiments, a terpene composition can be a mixture of terpene compounds derived from any suitable source, including naturally occurring terpenes and chemically synthesized terpenes, or mixtures of terpenes that may be commercially available. In various embodiments, a pharmaceutical composition can comprise a terpene composition having one of the various terpenoid compound profiles with the relative quantities illustrated in Table 2, below.

In various embodiments, a terpene composition can be configured to provide a therapeutic benefit. For example, a terpene composition configured to provide a sedative or anti-insomnia therapeutic benefit can comprise a pharmacologically effective amount and/or a therapeutically effective amount of a terpene selected from the group consisting of β-myrcene, linalool, nerolidol, and terpinolene. A terpene composition configured to provide an anxiolytic therapeutic benefit can comprise a pharmacologically effective amount and/or a therapeutically effective amount of a terpene selected from the group consisting of linalool and d-limonene. A terpene composition configured to provide an anti-convulsant therapeutic benefit can comprise a pharmacologically effective amount and/or a therapeutically effective amount of a terpene such as linalool.

In various embodiments, terpene composition can be configured to provide an amount of α-pinene that is pharmacologically effective to provide a bronchodilator effect. Inclusion of a pharmacologically effective amount of α-pinene in a pharmaceutical composition in accordance with various embodiments may be suitable to enhance the uptake of other therapeutic substances in the pharmaceutical composition, thereby enhancing their therapeutic effect or decreasing the concentration required to provide a pharmacological or therapeutic effect.

In various embodiments, a terpene composition used in a pharmaceutical composition can be formulated to provide a pharmacologically effective amount and/or a therapeutically effective amount of a terpenoid compound that provides a therapeutic benefit that is additive or a synergistic to a therapeutic benefit conferred by a cannabinoid composition in the same pharmaceutical composition. Expressed differently, a pharmaceutical composition in accordance with various embodiments can comprise both a cannabinoid composition and a terpene composition, each separately configured to provide a certain therapeutic benefit, wherein the inclusion of both provides an additive or synergistic therapeutic benefit as compared to the therapeutic benefit that may be achieved by a pharmaceutical composition having only the cannabinoid composition or the terpene composition.

Co-solvent

In various embodiments, a co-solvent used in a pharmaceutical composition can comprise an organic solvent such as an alcohol. In various embodiments, a co-solvent can be a monohydric or polyhydric alcohol. Various alcohols may be suitable, such as ethanol, propanol, polypropylene glycol, glycerol, polyethylene glycol, and the like, along with various mixtures thereof.

In accordance with various embodiments of the present disclosure, ethanol may be used as a co-solvent. In various embodiments, a *cannabis* composition such as a cannabinoid molecular distillate may be soluble in ethanol, and use of ethanol as a co-solvent may be suitable to provide a pharmaceutical composition with desired solution stability and aerosol performance in a pMDI system. However, a high ethanol content may be undesirable, as it can increase aerosol particle size and velocity and therefore reduce effective pulmonary delivery. In various embodiments, a pharmaceutical composition may be configured to minimize the required ethanol concentrations, for example, to reduce the potential for unpleasant taste sensations or to ensure appropriate aerosol particle size and maintain aerosol particle size below a certain size, while providing for a stable, solution-phase pharmaceutical composition. Accordingly, in various embodiments, a pharmaceutical composition can comprise less than about 25% ethanol, or less than about 20%, or less than about 19%, or less than about 18%, or less than about 17%, or less than about 16%, or less than about 15%, or less than about 14%, or less than about 13%, or less than about 12%, or less than about 11%, or less than about 10%, or less than about 9%, or less than about 8%, or less than about 7%, or less than about 6%, or less than about 7%, or less than about 6%, or less than about 5%, or less than about 4%, or less than about 3%, or less than about 2%, or less than about 1% ethanol by weight (w/w) of the composition. In various embodiments, a pharmaceutical composition can comprise from about 1% to about 20% ethanol, or from about 1% to about 5% ethanol, or from about 2% to about 8% ethanol, or from about 5% to 10% ethanol, or from about 7% to about 12% ethanol, or from about 10% to about 15% ethanol, or from about 13% to about 18% ethanol, or from about 15% to about 20% ethanol by weight (w/w) of the composition.

In various embodiments, a terpenoid compound such as d-limonene can function as a co-solvent, either in combination with an alcohol co-solvent or separately. Thus, in accordance with various embodiments of the present disclosure, the terpene component of a pharmaceutical composition can serve as a co-solvent and an alcohol co-solvent may not be required to provide solubility of the cannabinoid component in the pharmaceutical composition. In accordance with various embodiments and as described in greater detail below, the co-solvent composition and concentration may be adjusted to provide suitable cannabinoid composition solubility, pharmaceutical composition chemical and physical stability, and aerosol performance.

Propellant

In various embodiments, a propellant comprises a pharmacologically inert liquid with a boiling point of from about room temperature (25° C.) to about −25° C. which exerts a high vapor pressure at room temperature. Without wishing to be bound by theory, inclusion of a propellant in a pharmaceutical composition of the present disclosure provides for pressurization of the composition in a canister assembly of the pMDI system and upon activation of the pMDI system, the high vapor pressure of the propellant in the pMDI system forces a metered amount of pharmaceutical composition out through the metering valve and the propellant very rapidly vaporizes, dispersing the pharmaceutical composition as an aerosol. In various embodiments, a propellant may be a hydrofluorocarbon, for example, a hydrofluoroalkane such as 1,1,1,2-tetrafluoroethane (HFA 134a), 1,1,1,2,3,3,3-heptafluoropropane (HFA 227), or a mixture thereof.

A pharmaceutical composition in accordance with various embodiments can comprise from about 50% to about 75% propellant, or from about 55% to about 70% propellant, or from about 56% to about 69% propellant, or from about 57% to about 68% propellant, or from about 58% to about 67% propellant by weight (w/w) of the composition. In various embodiments, a pharmaceutical composition comprises less than about 75% propellant, or less than about 70% propellant, or less than about 69% propellant, or less than about 67% propellant by weight (w/w) of the composition. In various embodiments, a pharmaceutical composition comprises at least about 55% propellant, or at least about 58% propellant, or at least about 59% propellant, or at least about 60% propellant, or at least about 61% propellant, or at least about 62% propellant, or at least about 63% propellant, or at least about 64% propellant, or at least about 65% propellant, or at least about 66% propellant by weight (w/w) of the composition.

pMDI Devices and Systems

In various embodiments, a pharmaceutical composition is configured for delivery of an aerosolized dose of the pharmaceutical composition by a pressurized metered dose inhaler (pMDI) device. A pMDI device can comprise a delivery device consisting of a canister, a metering valve configured to sealably attach to a canister and to deliver a particular quantity of a composition contained within the canister (i.e., a metered dose) per actuation of the valve, and an actuator. A metering valve can be sealably attached to a canister to produce a canister assembly suitable to sealably contain a pressurized pharmaceutical composition. A pMDI device can also comprise a pharmaceutical composition contained within a sealed pMDI canister assembly.

In various embodiments, a pMDI system can comprise a plurality of pMDI canister assemblies or assembled pMDI devices (i.e., an assembled pMDI device including a filled canister assembly and an actuator), with each pMDI canister assembly or assembled pMDI device containing a different pharmaceutical formulation. Different pMDI canister assemblies or assembled pMDI devices containing different pharmaceutical formulations may be selected by a patient or a consumer in response to various factors, such as different desired therapeutic benefits, different sedative effects, different flavor profiles, and various combinations of the foregoing factors.

In various embodiments, an assembled pMDI device is configured to deliver the pharmaceutical composition in the form of droplets of a respirable size suitable for pulmonary administration. In various embodiments, a pMDI device, including the pharmaceutical composition, is configured to provide an aerosol particle size having a relatively uniform particle size distribution, for example, with substantially all, or at least about 90%, or at least about 80%, or at least about 70%, or at least about 60%, or at least about 50%, of the particles ranging between about 0.1 and about 25 microns, or between about 0.5 and about 10 microns, or between about 1.0 and about 5.0 microns. Particles larger than 25 microns may be deposited in the oropharyngeal cavity, while particles smaller than about 0.5 micron may fail to be deposited in the lungs and be lost due to exhalation. In various embodiments, the aerosol particle size produced by a pMDI device can be measured by cascade impaction and characterized by the mass median aerodynamic diameter (MMAD, i.e., the value for which 50% of the particles are larger or smaller). In various embodiments, the MMAD is between about 0.5 and about 10 microns, or between about 1.0 and about 5.0 microns.

In various embodiments, a pMDI device will comprise an actuator having an orifice with an orifice diameter. Preferably, the actuator orifice has a diameter in the range of from about 0.10 mm to about 0.70 mm, and more preferably in the range of from about 0.40 mm to about 0.70 mm. In various embodiments, the orifice diameter is in the range of from about 0.50 to about 0.60 mm.

In various embodiments, a metering valve used in a pMDI device can be configured to deliver a volume of a pharmaceutical composition in a range of from about 25 to about 100 microliters per actuation. In various embodiments, a pMDI device can be configured with a metering valve configured to deliver about a 50 microliter volume of a pharmaceutical composition.

In various embodiments, a pMDI device will comprise an actuator with an actuation or dose counter for counting the number of actuations of the system. The actuation or dose counter may be mechanical or electronic.

In various embodiments, a pMDI system can comprise a plurality of pharmaceutical formulations, with each pharmaceutical formulation comprising a different combination of one of a plurality of cannabinoid compositions and/or one of a plurality of terpene compositions. In various embodiments, each of the cannabinoid composition and the terpene composition in a pharmaceutical composition may provide a different therapeutic benefit. In various embodiments, a cannabinoid composition and a terpenoid composition may each provide the same therapeutic benefit. In such embodiments, the therapeutic benefit provided by each may be additive or synergistic.

In various embodiments, a system can comprise a first pharmaceutical composition configured to provide a first therapeutic benefit and a second therapeutic benefit, and a second pharmaceutical composition configured to provide a first therapeutic benefit and a third therapeutic benefit. For example, in various embodiments, two different pharmaceutical compositions may comprise the same cannabinoid composition but have different terpene compositions, such as a terpene composition configured to provide a sedative (i.e., second) therapeutic benefit and a terpene composition configured to provide an enhanced alertness (i.e., third) therapeutic effect. The cannabinoid composition may provide a separate therapeutic benefit, such as a systemic analgesic (i.e., first) therapeutic benefit. In this manner, a patient or consumer can select a pharmaceutical composition having cannabinoid composition configured to provide an analgesic therapeutic benefit with a desired sedative or enhanced alertness therapeutic benefit in response to a sedation preference.

Moreover, in various embodiments, a plurality of terpene compositions can be configured to provide a particular therapeutic benefit, such as a sedative therapeutic benefit, with each of the plurality of terpene compositions providing a distinct flavor profile, enabling a consumer to select a pharmaceutical composition providing a particular therapeutic benefit, from among a plurality of pharmaceutical compositions configured to provide the same desired therapeutic effect, in response to a particular flavor preference.

In accordance with various embodiments, each of plurality of pharmaceutical compositions may be packaged in a pMDI canister. In various embodiments, different pharmaceutical compositions in different pMDI canisters may be user-interchangeable with a single actuator device, or a user may simply select a different pharmaceutical composition, with each composition packaged in a pMDI canister and assembled to a separate actuator device. Thus, in accordance with various embodiments, a pMDI system is provided that can permit a consumer or patient to select from a plurality of pharmaceutical compositions based on at least one of a desired therapeutic benefit, a desired sedative effect, and a desired flavor profile.

Methods of Formulation

Compositions for aerosol administration via pMDIs can be formulated as solutions or suspensions. Solution compositions can offer several advantages, including that they can be more convenient to manufacture being completely dissolved in the propellant vehicle and they avoid the physical stability problems associated with suspension compositions. However, solution compositions comprising cannabinoid compounds at suitable concentrations while providing appropriate aerosol particle characteristics can be challenging to achieve, particularly for *cannabis*-extract derived formulations, and compositions can quickly separate, forming sediments or emulsions and leading to clogging or other performance problems that can frustrate a user, such as by interfering with consistent or expected dosing or by preventing access to the product altogether. Moreover, chemical instability leading to the degradation of therapeutic substance components and producing a change in product efficacy can also be problematic for some compositions.

As described above, a co-solvent such as ethanol can be used to provide enhanced cannabinoid composition solubility in a pharmaceutical composition for administration by pMDI; however, increasing ethanol concentration can produce increased aerosol particle sizes, which may be undesirable.

Surprisingly, it was discovered that the use of terpene compositions in the formulations of the present disclosure permitted achieving stable solutions of a cannabinoid composition in propellant at lower concentrations of co-solvent than for formulations lacking terpene solutions. Expressed differently, inclusion of a terpene composition in a pharmaceutical composition can increase the solubility of a cannabinoid composition in the pharmaceutical composition. In various embodiments, inclusion of a terpene composition in a pharmaceutical composition can provide a for a stable pharmaceutical composition solution comprising a first concentration of a cannabinoid composition and a decreased co-solvent concentration relative to a pharmaceutical composition lacking a terpene composition.

In various embodiments, a surfactant optionally may be added to lower the surface and interfacial tension between the cannabinoid composition, the propellant, co-solvent, and the terpene composition, if present. A surfactant may be any suitable, non-toxic compound which is non-reactive with the pharmaceutical composition components and which substantially reduces the surface tension and/or interfacial tension between the cannabinoid composition, the propellant, co-solvent, and or terpene composition. However, various formulations disclosed herein do not require a surfactant to produce and/or maintain a stable pharmaceutical composition solution under normal operating conditions, and in various embodiments a pharmaceutical composition may be surfactant-free.

The present disclosure also provides a method of formulating a pharmaceutical composition having a stable aerosol solution formulation. In various embodiments, a method of formulating a pharmaceutical composition comprises mixing a cannabinoid composition with a co-solvent to produce a first solution. The first solution is then mixed with a terpene composition to produce a second solution. The second solution can be placed in an MDI canister and then mixed with propellant in a two-stage pressure fill pMDI manufacturing method, or the second solution can be mixed with propellant and injected into a precrimped pMDI canister using a single-stage pressure fill approach. In various embodiments, the proportions of cannabinoid composition, co-solvent, terpene composition, and propellant used in a pharmaceutical composition may be adjusted to produce a pharmaceutical composition that is a stable solution under various storage and handling conditions. A finished pharmaceutical composition can be evaluated optically in accordance with various embodiments following formulation to ensure that the finished pharmaceutical composition is not subject to separation or precipitation. For example, in various embodiments, a cannabinoid composition, co-solvent, and terpene composition mixture may be placed in a transparent glass jar suitable for sealing with a metering valve or similar component through which propellant may be added to the mixture and capable of withstanding typical pMDI pressures. Propellant may be gradually added to the mixture in the sealed jar and monitored visually to assess solubility of the mixture in the propellant. In various embodiments, a soluble formulation will have a homogenous optically clear appearance, while an insoluble formulation will appear cloudy due to the presence of an emulsion and/or liquid separation will occur due to immiscibility. In various embodiments, the homogeneity of a pharmaceutical composition formulation can be monitored visually during formulation and for a period of time following formulation to ensure solubility.

In various embodiments, if a pharmaceutical composition with a particular formulation undergoes separation following formulation, as determined visually by assessment of the stability of the formulation in a pressurized glass jar, the composition may be reformulated, such as by increasing the proportion of the co-solvent and/or the terpene composition relative to the cannabinoid composition and repeating the process outlined above.

In various embodiments, the ratio of propellant to the mixture of cannabinoid composition, co-solvent, and terpene composition components can be titrated to produce a soluble pharmaceutical composition. In various embodiments, the proportion of each of a cannabinoid composition, co-solvent, terpene composition, and propellant in a pharmaceutical composition may be separately titrated to produce a soluble pharmaceutical composition.

For example, for a pharmaceutical composition formulated in accordance with various embodiments of the present disclosure, a cannabinoid composition can comprise a cannabinoid molecular distillate at a concentration of from about 14% to about 19% by weight (w/w) of the composition, a co-solvent can comprise ethanol at a concentration of from about 14% to about 19% by weight (w/w) of the composition, a terpene composition can comprise a terpene mix at a concentration of from about 0.5% to about 4.0% by weight (w/w) of the composition, and a propellant can comprise HFA 134a at a concentration of from about 58% to about 72% by weight (w/w) of the composition.

Particle Size (Aerosol Performance)

In accordance with various embodiments, the formulation of a pharmaceutical composition can be configured to provide desired aerosol performance characteristics during delivery by a metered dose inhaler system. Factors such as the viscosity of the pharmaceutical composition and the various components thereof, and the interaction of the pharmaceutical composition with the pMDI device during actuation based on various factors such as the nozzle size and shape and the mouthpiece configuration can influence aerosol characteristics during administration of the pharmaceutical composition. In various embodiments, a pharmaceutical composition can be configured to provide the desired aerosol performance characteristics when used with a pMDI device configured with various parameters provided elsewhere herein.

Stability

In various embodiments, the pharmaceutical compositions of the present disclosure may be physically and/or chemically stable under periods of storage and/or thermal stresses of up to about 55° C. for up to about six hours. The ability of a composition to withstand prolonged storage or thermal stress can be measured, for example, by subjecting a composition to storage at elevated temperatures and subsequently measuring fine particle fraction of the composition upon actuation of the delivery system. An instrument such as an Andersen Cascade Impactor can be used to measure the fine particle fraction (FPF), or the mass of aerosol particles with aerodynamic diameters that are less than approximately 5 microns.

In various embodiment, a mass of particles of a pharmaceutical composition subjected to temperatures up to about 45° C. for up to about six hours exhibits a FPF that varies from the FPF of a mass of similar particles for the same pharmaceutical composition held at room temperature by less than about 25%, or less than about 20%, or less than about 15%, or less than about 10%.

In various embodiment, a mass of particles of a pharmaceutical composition subjected to temperatures up to about 55° C. for up to about six hours exhibits a FPF that varies from the FPF of a mass of similar particles for the same pharmaceutical composition held at room temperature by less than about 25%, or less than about 20%, or less than about 15%, or less than about 10%.

In various embodiments, a pharmaceutical composition of the present disclosure can be characterized by the chemical stability of the pharmaceutical composition, including the cannabinoid composition and/or the terpenoid composition that comprises the pharmaceutical composition. Without wishing to be bound by theory, it is believed that several factors can influence the chemical stability of a pharmaceutical composition, such as the composition, stability, and/or interactions of the pharmaceutical composition components.

Chemical stability can be assessed using various techniques well known in the art, such as high performance liquid chromatography (HPLC) and/or gas chromatography-mass spectrometry (GC-MS).

In various embodiments, the pharmaceutical compositions of the present disclosure do not exhibit substantial degradation of the cannabinoid compounds comprising the cannabinoid composition or the terpenoid compounds comprising the terpenoid composition after being stored at temperatures of up to about 40° C. for up to about three months. In various embodiments, the cannabinoid composition and/or terpenoid composition is within about 75%, or within about 80%, or within about 85%, or within about 90%, or within about 95%, or within about 98% of the starting cannabinoid composition and/or terpenoid composition by weight following a storage period of three months at temperatures of up to about 40° C.

In various embodiments, a pharmaceutical composition may be formulated to provide a stable solution following mixing and pressurization of the composition in a pMDI canister. A stable solution may not be subject to physical separation or precipitation of composition components during normal product handling and use, or during extended storage and handing periods and conditions such as a product may be subject to during packaging, warehousing, shipping, handling, and the like. In various embodiments, a pharmaceutical composition may remain a stable solution for storage and handling periods of up to about one month, or up to about three months, or up to about six months, or up to about 9 months, or up to about 12 months, under a variety of temperature conditions including temperatures of up to about 30° C., or about 40° C., or about 45° C., or about 50° C., for up to about 1 hour, or up to about 3 hours, or up to about 12 hours, or up to about 24 hours. In various embodiments, the stability of a pharmaceutical composition can be assessed optically. In various embodiments, the stability of a pharmaceutical composition can be assessed based on performance of the pMDI system over the course of simulated or accelerated life cycle testing. For example, in various embodiments, a pMDI system may be evaluated for delivery of a consistent mass of the pharmaceutical composition contained within the system, such as delivery of a 50 mg mass at the first actuation, the second actuation, the third actuation, and the nth actuation, wherein n may be, for example, the designed maximum number of actuations. In various embodiments, a pharmaceutical formulation and a pMDI system may provide at least about 75%, or at least about 80%, or at least about 85%, or at least about 90%, or at least about 95%, or at least about 99% delivery consistency by mass per actuation for the first actuation compared to the nth actuation. Similarly, in various embodiments, other physical attributes of the delivered aerosol, such as the FPF or the MMAD may be evaluated for consistent performance of a pMDI system and pharmaceutical formulation over a simulated or accelerated life cycle test of the system.

Methods of Treatment

The pharmaceutical compositions of the present invention can be used to treat a variety of medical conditions, including without limitation nausea and vomiting associated with cancer chemotherapy, muscle spasticity, pain, anorexia associated with AIDS wasting syndrome, anorexia associated with cancer chemotherapy, epilepsy, glaucoma, Chrohn's disease, inflammatory bowel disease, multiple sclerosis, Amylotrophic Lateral Sclerosis (ALS), muscular dystrophy, bronchial asthma, post-traumatic stress disorder, mood disorders, and migraine headaches.

In various embodiments, a pharmaceutical composition and a pMDI system may be configured to deliver a pharmacologically effective amount of a cannabinoid and/or a terpene to a patient in need thereof. As used herein, a pharmacologically effective amount of a compound is an amount sufficient to produce a detectable concentration of the substance, a metabolite of the substance, or some other substance produced in response to administration of an amount of a compound, in a physiological sample obtained from a treated patient at a certain time interval following administration of the amount (or dose). A physiological sample can comprise, for example, a blood serum sample.

In various embodiments, a pharmaceutical composition and a pMDI system may be configured to deliver a therapeutically effective amount of a cannabinoid and/or a terpene to a patient in need thereof. As used herein, a therapeutically effective amount of a substance is an amount delivered to a patient sufficient to elicit a required or desired therapeutic and/or prophylactic response, as the particular treatment context may require. In various embodiments, a therapeutically effective amount may be the amount of a substance sufficient to provide the patient with an objectively or subjectively perceptible effect or therapeutic benefit relative to a treated condition. In various embodiments, the presence of a therapeutically effective amount of both a cannabinoid and a terpene are necessary and sufficient to produce a therapeutic benefit.

In various embodiments, a pharmacologically effective amount of a cannabinoid or terpenoid compound in a pharmaceutical composition following administration to a human patient may be determined clinically based on objectively measurable data. A pharmacologically effective amount of a compound can be determined at a particular time interval following administration of a composition to a patient, for example, by collection of a physiological sample such as a blood sample from the treated patient. A blood sample can be collected from minutes after administration of a pharmaceutical composition to hours or days after administration.

In various embodiments, a physiological sample such as a blood sample can be collected at about 1 minute, or about 2 minutes, or about 3 minutes, or about 4 minutes, or about 5 minutes, or about 10 minutes, or about 15 minutes, or about 20 minutes, or about 30 minutes, or about 60 minutes, or about 120 minutes following administration of a pharmaceutical composition. In various embodiments, a pharmacologically effective amount of a cannabinoid or a terpene measured for a blood sample collected following administration of a pharmaceutical composition can be a blood serum concentration of at least about 0.5 ng/ml, or about 1.0 ng/ml, or about 2.0 ng/ml, or about 3.0 ng/ml, or about 4.0 ng/ml, or about 5.0 ng/ml, or about 6.0 ng/ml, or about 7.0 ng/ml, or about 8.0 ng/ml, or about 9.0 ng/ml, or about 10.0 ng/ml, or about 20 ng/ml, or about 30 ng/ml, or about 50 ng/ml, or about 70 ng/ml, or about 100 ng/ml for the subject compound or a metabolite thereof.

EXAMPLES

Example 1

Cannabinoid Molecular Distillate Preparation

*Cannabis* extracts were produced by extracting *cannabis* flower material using supercritical fluid extraction. Following extraction, the extracts were dissolved in ethanol and winterized using standard procedures to produce winterized extracts. Winterized extracts were decarboxylated and subjected to molecular distillation using a short path distillation apparatus (Pope, Inc., Saukville, Wis.) to produce cannabinoid molecular distillates. Cannabinoid molecular distillate samples were sent to a third-party analytical service provider (Desert Valley Testing, Phoenix, Ariz.) to assess the quality of the distillates and the concentrations of various cannabinoid compounds. Measured relative concentrations of various cannabinoid compounds for cannabinoid molecular distillates used to prepare pharmaceutical compositions in accordance with various embodiments of the present disclosure are shown below in Table 1.

As shown in Table 1, the tested cannabinoid compositions did not include measurable CBD. THC was the dominant cannabinoid compound, ranging from about 70% to about 90% of the total cannabinoids by weight. THCA was detectable in only a couple of the samples since the extracts were decarboxylated during the extraction and distillation process. THCV was present in each of the extracts at about 0.5% or higher. CBG concentrations ranged from about 1% (1.48%) to about 3% (2.31%), CBN concentrations ranged from about 1% (0.98%) to about 5% (4.44%), and CBC concentrations ranged from about 2% (1.84%) to about 11% (10.57%).

mulated based on the terpene profiles of different prominent *Cannabis sativa* and *Cannabis indica* strains.

The *Cannabis sativa* strains used as a basis for terpene composition formulations were "Candy Jack," "Jack Herer," "Sour Diesel," and "Super Lemon Haze." The pharmaceutical compositions comprising these terpene compositions were classified as "Daytime" product formulations configured to provide cannabinoid compound therapeutic benefits with a low sedative effect. These "Daytime" terpene compositions include dominant terpenes other than β-myrcene, linalool, or d-limonene, as shown in detail below in Table 2. For example, terpinolene and β-caryophyllene are the dominant terpenes in the "Jack Herer" terpene composition, α-pinene and (−)-β-pinene are the dominant terpenes in the "Sour Diesel" terpene composition, and terpinolene, β-caryophyllene, and α-humulene are the dominant terpenes in the "Super Lemon Haze" product formulation. β-myrcene, linalool, and d-limonene, while variously present in each, are present in comparatively low levels.

*Cannabis indica* strains used as a basis for terpene composition formulations were "Granddaddy Purple," "King Louie XIII OG," "OG Kush," and "Paris OG." The pharmaceutical compositions comprising these terpene compo-

TABLE 1

Relative concentrations of individual cannabinoid compounds in various cannabinoid compositions.

| Sample | CBDA | CBG | CBD | THCV | CBN | THC | CBC | THCA | Total Cannabs. |
|---|---|---|---|---|---|---|---|---|---|
| 3 | 0.00 | 2.07 | 0.00 | 0.57 | 3.08 | 88.12 | 1.84 | 0.00 | 95.68 |
| 13 | 0.00 | 1.91 | 0.00 | 0.54 | 2.12 | 78.48 | 5.73 | 0.00 | 88.42 |
| 10A | 0.00 | 1.48 | 0.00 | 0.51 | 2.57 | 73.84 | 8.12 | 0.00 | 86.53 |
| 10L | 0.00 | 2.29 | 0.00 | 0.00 | 4.44 | 70.45 | 9.22 | 0.00 | 86.41 |
| 12A | 0.00 | 2.23 | 0.00 | 0.56 | 2.46 | 83.06 | 4.03 | 0.00 | 92.35 |
| 12B | 0.00 | 2.31 | 0.00 | 0.55 | 2.38 | 80.65 | 3.89 | 0.00 | 89.78 |
| Aft 9/9 | 0.00 | 1.67 | 0.00 | 0.65 | 2.73 | 80.80 | 10.57 | 0.00 | 96.42 |
| B4 9/9 | 0.00 | 1.80 | 0.00 | 0.51 | 2.89 | 80.37 | 4.43 | 0.00 | 90.00 |
| C14 | 0.00 | 1.89 | 0.00 | 0.55 | 3.32 | 80.96 | 4.72 | 0.00 | 91.44 |
| 10B | 0.00 | 1.95 | 0.00 | 0.56 | 3.31 | 87.39 | 5.34 | 0.89 | 99.43 |
| 16 | 0.00 | 1.81 | 0.00 | 0.64 | 3.34 | 89.63 | 4.00 | 0.40 | 99.82 |
| 151 | 0.00 | 1.48 | 0.00 | 0.62 | 2.58 | 75.70 | 2.79 | 0.00 | 83.17 |
| 152 | 0.00 | 1.60 | 0.00 | 0.68 | 3.03 | 83.00 | 3.33 | 0.00 | 91.64 |
| J3 | 0.00 | 1.62 | 0.00 | 0.64 | 0.98 | 75.77 | 4.66 | 0.00 | 83.67 |
| Average | 0.00 | 1.87 | 0.00 | 0.54 | 2.80 | 80.59 | 5.19 | 0.09 | 91.05 |

Example 2

Formulation of Products with Different Sedative Effects

The *cannabis* extract cannabinoid compound molecular distillates described in Example 1 were used to prepare pharmaceutical compositions having different terpene compositions. The various terpene compositions used were forsitions were classified as "Nighttime" product formulations configured to provide cannabinoid compound therapeutic benefits combined with a high sedative effect. The terpene profiles of each terpene composition for the "Nighttime" production formulations included a high proportion of β-myrcene, linalool, and d-limonene with varying levels of other terpenoid compounds.

TABLE 2

Relative concentrations of individual terpenoid compounds in various terpene compositions in accordance with various embodiments.

| | Candy Jack | Jack Herer | Jack Herer (2) | Sour Diesel | Super Lemon Haze | Granddaddy Purple | King Louie XIII | OG Kush | Paris OG | Paris OG II |
|---|---|---|---|---|---|---|---|---|---|---|
| α-pinene | 2.67 | 2.98 | 2.95 | 57.98 | 0.71 | 3.69 | 2.48 | 0.00 | 2.44 | 2.67 |
| camphene | 0.00 | 0.00 | 0.00 | 1.18 | 0.00 | 0.00 | 0.00 | 0.22 | 0.00 | 0.00 |
| (−)-β-pinene | 0.00 | 0.00 | 0.00 | 32.84 | 0.64 | 0.32 | 6.33 | 1.98 | 4.50 | 6.99 |
| β-myrcene | 4.06 | 0.00 | 0.00 | 0.31 | 5.17 | 5.90 | 11.54 | 17.77 | 8.74 | 13.71 |
| δ-3-carene | 0.00 | 0.00 | 0.00 | 0.00 | 0.00 | 0.00 | 0.00 | 0.00 | 0.00 | 0.00 |
| d-limonene | 1.60 | 4.63 | 5.55 | 5.07 | 0.66 | 0.24 | 23.49 | 11.63 | 23.81 | 21.61 |
| α-terpene | 0.00 | 0.00 | 0.00 | 0.00 | 0.00 | 0.00 | 0.00 | 0.00 | 0.00 | 0.00 |

TABLE 2-continued

Relative concentrations of individual terpenoid compounds in various terpene compositions in accordance with various embodiments.

| | Candy Jack | Jack Herer | Jack Herer (2) | Sour Diesel | Super Lemon Haze | Granddaddy Purple | King Louie XIII | OG Kush | Paris OG | Paris OG II |
|---|---|---|---|---|---|---|---|---|---|---|
| P-cymene | 0.00 | 0.23 | 0.00 | 0.00 | 0.00 | 0.00 | 0.00 | 0.00 | 0.00 | 0.00 |
| eucalyptol | 0.00 | 0.00 | 0.00 | 0.00 | 0.00 | 0.00 | 0.00 | 0.00 | 0.00 | 0.00 |
| ocimene | 0.00 | 0.00 | 0.00 | 0.00 | 0.00 | 0.00 | 0.00 | 0.00 | 0.00 | 0.00 |
| γ-terpinene | 0.00 | 0.13 | 0.30 | 0.00 | 0.00 | 0.00 | 0.00 | 0.00 | 0.00 | 0.00 |
| terpinolene | 6.03 | 19.53 | 33.91 | 0.00 | 20.41 | 28.99 | 3.85 | 1.19 | 3.85 | 4.26 |
| linalool | 7.56 | 1.92 | 1.25 | 0.00 | 0.37 | 77.23 | 10.25 | 2.96 | 10.38 | 11.61 |
| (−)-isopulegol | 0.00 | 0.00 | 0.00 | 0.00 | 0.00 | 0.00 | 0.00 | 0.00 | 0.00 | 8.47 |
| geraniol | 0.70 | 0.00 | 0.00 | 0.00 | 0.00 | 0.00 | 0.00 | 0.00 | 0.00 | 0.00 |
| β-caryophyllene | 40.51 | 22.07 | 19.12 | 0.27 | 39.84 | 8.39 | 24.39 | 13.66 | 24.40 | 24.99 |
| α-humulene | 0.21 | 2.00 | 1.71 | 0.00 | 22.14 | 10.40 | 2.19 | 0.00 | 2.22 | 1.51 |
| nerolidol | 0.00 | 0.00 | 0.00 | 0.00 | 0.00 | 0.00 | 0.00 | 2.11 | 0.00 | 0.00 |
| (−)-guaiol | 0.00 | 0.00 | 0.00 | 0.00 | 0.00 | 0.00 | 0.00 | 0.00 | 0.00 | 0.00 |
| (−)-α-bisabolol | 0.00 | 0.00 | 0.00 | 0.00 | 0.00 | 0.00 | 0.00 | 0.00 | 0.00 | 0.00 |
| (−)-caryophylene oxide | 8.93 | 2.84 | 0.00 | 0.25 | 0.29 | 0.21 | 1.89 | 0.47 | 3.76 | 0.78 |
| sabinene | 0.70 | 0.00 | 0.00 | 0.00 | 0.89 | 1.02 | 2.02 | 3.07 | 1.53 | 2.38 |
| α-phellandrene | 0.00 | 0.00 | 0.00 | 0.00 | 0.00 | 0.00 | 0.34 | 0.39 | 0.30 | 0.37 |
| fenchol | 0.00 | 0.00 | 0.00 | 0.00 | 0.13 | 0.00 | 0.00 | 0.43 | 0.00 | 0.00 |
| camphor | 0.00 | 0.00 | 0.00 | 0.00 | 0.00 | 0.00 | 0.00 | 0.00 | 0.00 | 0.00 |
| isoboreol | 2.89 | 0.00 | 0.00 | 0.00 | 0.00 | 0.00 | 0.00 | 0.00 | 0.00 | 0.00 |
| menthol | 0.57 | 0.00 | 0.00 | 0.00 | 0.00 | 0.00 | 0.00 | 0.00 | 0.00 | 0.00 |
| borneol | 4.93 | 0.00 | 0.00 | 0.00 | 0.00 | 0.00 | 0.00 | 0.00 | 0.00 | 0.00 |
| terpineol | 0.23 | 0.00 | 0.19 | 0.00 | 0.00 | 0.00 | 0.20 | 0.36 | 0.85 | 0.23 |
| (+)-pulegone | 0.00 | 0.00 | 0.00 | 0.00 | 0.00 | 0.00 | 0.00 | 0.00 | 0.00 | 0.00 |
| geranyl acetate | 0.00 | 0.00 | 0.00 | 0.00 | 0.00 | 0.00 | 0.00 | 0.16 | 0.00 | 0.00 |
| valencene | 0.00 | 0.00 | 0.00 | 0.00 | 0.00 | 0.00 | 0.00 | 0.00 | 0.00 | 0.00 |

Example 3

Formulation of Other Terpene Mixes

Different terpene mixes were prepared and tested with a panel of blind tasters to identify terpene mixes that provided agreeable flavor profiles.

Five different terpenes—myrcene, carvone, limonene, terpinolene, and pinene—were combined in equal amounts in various combinations of two, three, and four terpenes to create test terpene mixes. A test terpene mix comprising a combination of equal quantities of all five terpenes was also created. Additional pre-mixed terpene flavors including "Peppermint," "Tangerine," "Grapefruit," "Lime," and "Strawberry Lemonade" were included in the blind taste testing. All terpene mixes were assigned unique identifier codes, mixed into a formulation comprising either propellant and ethanol or propellant, ethanol, and CBD in proportions suitable for use in pharmaceutical formulation in accordance with various embodiments of the present disclosure, and administered to the test panel.

Of the numerous terpene mixes tested, six were selected as preferred based on their agreeableness and for masking the flavor and/or burn experienced by the tasters due to inhalation of the formulation and the various components thereof. Another seven were identified that were acceptable. The preferred terpene mixes included: Peppermint, Strawberry Lemonade, terpinolene+α-pinene, d-limonene+α-pinene, myrcene+carvone+d-limonene, and d-limonene+terpinolene+α-pinene.

Example 4

Pharmaceutical Composition Formulation and Packaging

A *cannabis* extract was used to prepare a cannabinoid composition as described in Example 1. The cannabinoid composition was used to prepare a pMDI pharmaceutical composition comprising 1,000 mg of cannabinoid composition. The cannabinoid composition was mixed with 1,000 mg of USP-grade ethanol until dissolved. Next, 50 mg of a terpene composition was added to the cannabinoid composition and ethanol solution and mixed. The resultant solution was placed in a pMDI canister, a 50 microliter valve was installed and crimped to the canister, and 3.75 g of HFA 134a was added to the canister via the valve using a Pamasol pMDI filling station (Pamasol Willi Mäder AG, Pfäffikon, Switzerland) to produce a pMDI canister comprising a pharmaceutical composition in accordance with the present disclosure. The canister was assembled to an actuator having a 0.58 mm nozzle orifice diameter, and the assembled pMDI system tested to ensure that 50 microliter metered doses of the pharmaceutical composition were delivered per actuation of the system (based on measured canister weight), whereby approximately 10 mg of cannabinoid compound medicine was delivered per actuation.

Example 5

Additional Pharmaceutical Composition Formulation Examples

Pharmaceutical compositions were formulated using the same *cannabis* extract cannabinoid compound molecular distillate, prepared as described in Example 1, or CBD isolate, and various terpene compositions having the terpenoid profiles shown below in Table 3. The terpenoid profiles for "Jack Herer" and "Granddaddy Purple" mixes shown in Table 3 are the same as those in Table 2. Formulations were determined in accordance with the methods described herein to produce soluble pharmaceutical compositions having the formulations described below.

TABLE 3

Relative concentrations of individual terpenoid compounds in various terpene compositions in accordance with various embodiments.

| | Jack Herer | Granddaddy Purple | Strawberry | Girl Scout Cookies | Bubble Gum |
|---|---|---|---|---|---|
| α-pinene | 2.98 | 3.69 | 43.14 | 2.29 | 60.79 |
| camphene | 0.00 | 0.00 | 0.00 | 0.00 | 0.26 |
| (−)-β-pinene | 0.00 | 0.32 | 4.52 | 0.34 | 6.38 |
| β-myrcene | 0.00 | 5.90 | 2.13 | 4.35 | 3.08 |
| δ-3-carene | 0.00 | 0.00 | 0.00 | 0.00 | 0.00 |
| d-limonene | 4.63 | 0.24 | 0.00 | 25.26 | 6.40 |
| α-terpinene | 0.00 | 0.00 | 0.00 | 0.00 | 0.00 |
| P-cymene | 0.23 | 0.00 | 0.00 | 0.00 | 0.00 |
| eucalyptol | 0.00 | 0.00 | 0.00 | 0.00 | 0.00 |
| ocimene | 0.00 | 0.00 | 0.00 | 0.00 | 0.00 |
| γ-terpinene | 0.13 | 0.00 | 0.00 | 0.00 | 0.00 |
| terpinolene | 19.53 | 28.99 | 0.00 | 4.52 | 0.00 |
| linalool | 1.92 | 77.23 | 0.00 | 12.14 | 0.00 |
| (−)-isopulegol | 0.00 | 0.00 | 0.00 | 0.00 | 0.00 |
| geraniol | 0.00 | 0.00 | 0.00 | 0.00 | 0.00 |
| β-caryophyllene | 22.07 | 8.39 | 2.29 | 27.23 | 2.94 |
| α-humulene | 2.00 | 10.40 | 0.18 | 2.59 | 0.24 |
| nerolidol | 0.00 | 0.00 | 0.00 | 0.00 | 0.00 |
| (−)-guaiol | 0.00 | 0.00 | 0.00 | 0.00 | 0.00 |
| (−)-α-bisabolol | 0.00 | 0.00 | 0.00 | 0.29 | 0.00 |
| (−)-caryophylene oxide | 2.84 | 0.21 | 0.00 | 6.21 | 0.20 |
| sabinene | 0.00 | 1.02 | 0.37 | 0.75 | 0.55 |
| α-phellandrene | 0.00 | 0.00 | 0.00 | 0.18 | 0.00 |
| fenchol | 0.00 | 0.00 | 0.00 | 0.00 | 0.00 |
| camphor | 0.00 | 0.00 | 0.00 | 0.00 | 0.00 |
| isoboreol | 0.00 | 0.00 | 0.00 | 0.00 | 0.00 |
| menthol | 0.00 | 0.00 | 0.00 | 0.00 | 0.00 |
| borneol | 0.00 | 0.00 | 0.00 | 0.00 | 0.00 |
| terpineol | 0.00 | 0.00 | 0.48 | 0.46 | 0.00 |
| (+)-pulegone | 0.00 | 0.00 | 0.00 | 0.00 | 0.00 |
| geranyl acetate | 0.00 | 0.00 | 0.00 | 0.00 | 0.00 |
| valencene | 0.00 | 0.00 | 0.00 | 0.00 | 0.00 |

Cannabinoid compositions were mixed with ethanol co-solvent in equal proportions on a weight to weight basis in transparent glass pMDI jars until dissolved. The terpene compositions listed in Table 3 where then added to cannabinoid composition and ethanol solutions and mixed until dissolved. The jars were then sealed with a metering valve and HFA 134a was injected into the jar and mixed with the cannabinoid composition, ethanol, and terpenoid composition solution. The solubility of the mixtures was monitored during propellant injection, and injection addition was stopped when evidence of insolubility or separation became apparent on visual inspection through the transparent jar. Propellant was purged via the valve until the mixture again became soluble, and the maximum weight of propellant that could be used with each formulation while providing a soluble formulation was determined. The weights and proportions of each pharmaceutical composition component for the various formulations determined in this manner are shown in Tables 4 and 5.

TABLE 4

Formulations of soluble pMDI pharmaceutical compositions having various terpene compositions and 1.00 g total cannabinoid composition per pMDI.

| | Strawberry/ Distillate | Strawberry/ CBD | Girl Scout Cookies/ Distillate | Bubble Gum/ Distillate | Bubble Gum/ CBD | Jack Herer/ Distillate | Granddaddy Purple/ Distillate |
|---|---|---|---|---|---|---|---|
| Cannabinoid composition | 1.00 g (16.2%) | 1.00 g (17.1%) | 1.00 g (16.3%) | 1.00 g (15.8%) | 1.00 g (16.0%) | 1.00 g (17.8%) | 1.00 g (16.8%) |
| Ethanol | 1.00 g (16.2%) | 1.00 g (17.1%) | 1.00 g (16.3%) | 1.00 g (15.8%) | 1.00 g (16.0%) | 1.00 g (17.8%) | 1.00 g (16.8%) |
| Terpene composition | 0.0900 g (1.45%) | 0.0900 g (1.53%) | 0.150 g (2.44%) | 0.150 g (2.36%) | 0.150 g (2.40%) | 0.165 g (2.94%) | 0.165 g (2.77%) |
| HFA 134a | 6.19 g (66.2%) | 5.84 g (64.2%) | 6.15 g (65.0%) | 6.35 g (66.1%) | 6.25 g (65.6%) | 5.62 g (61.4%) | 5.97 g (63.7%) |

TABLE 5

Formulations of soluble pMDI pharmaceutical compositions having various terpene compositions and 0.500 g total cannabinoid composition per pMDI.

| | Strawberry/ Distillate | Strawberry/ CBD | Girl Scout Cookies/ Distillate | Bubble Gum/ Distillate | Bubble Gum/ CBD | Jack Herer/ Distillate | Granddaddy Purple/ Distillate |
|---|---|---|---|---|---|---|---|
| Cannabinoid composition | 0.500 g (16.4%) | 0.500 g (17.0%) | 0.500 g (16.8%) | 0.500 g (15.8%) | 0.500 g (16.3%) | 0.500 g (18.6%) | 0.500 g (17.4%) |
| Ethanol | 0.500 g (16.4%) | 0.500 g (17.0%) | 0.500 g (16.8%) | 0.500 g (15.8%) | 0.500 g (16.3%) | 0.500 g (18.6%) | 0.500 g (17.4%) |
| Terpene composition | 0.0450 g (1.48%) | 0.0450 g (1.53%) | 0.0750 g (2.52%) | 0.0750 g (2.36%) | 0.0750 g (2.40%) | 0.0825 g (3.06%) | 0.0825 g (2.61%) |
| HFA 134a | 3.05 g (65.7%) | 2.95 g (64.5%) | 2.98 g (63.9%) | 3.18 g (66.1%) | 3.08 g (65.6%) | 2.68 g (59.7%) | 2.88 g (63.7%) |

As shown in Tables 4 and 5, the proportions of cannabinoid composition and ethanol in the various formulations ranged from 15.8% to 18.6%. The proportions of terpene composition in the various formulations ranged from 1.45% to 3.06%. The proportions of HFA 134a in the various formulations ranged from 59.7% to 66.2%. The lowest proportion of terpene composition was observed for a peppermint formulation having a CBD isolate cannabinoid composition, with a terpene composition concentration of 0.97%. The same peppermint CBD isolate formulation had a propellant concentration of 66.6%.

Example 6

Aerosol Particle Size Testing

The mass mean aerodynamic diameter (MMAD) is determined using an instrument such as an Aerosizer DSP Model 3225 Particle Size Analyzer (Amherst Process Instrument, Inc., Amherst, Mass.). A pharmaceutical composition in accordance with various embodiments is prepared, packaged in a pMDI system, and introduced into the instrument via an actuator. The instrument then uses time-of-flight measurements to determine the aerodynamic diameter of the aerosol particles. Particle density is assumed to be an arbitrary 1 g/cm3 for the purposes of these measurements.

Fine Particle Fraction (FPF) is measured using an instrument such as an Anderson Cascade Impactor. A pharmaceutical composition in accordance with various embodiments is introduced into the instrument by actuation of the pMDI system. The stages are selected to collect particles with various effective cutoff diameters (ECD). The mass deposited on each stage is determined gravimetrically. Three replicate runs are performed for each sample and the values are averaged. FPF is then expressed as a fraction of the total mass introduced into the instrument.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Compositions, systems, and methods are provided herein. In the detailed description herein, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. An inhaler system consisting essentially of an actuator, a user interchangeable canister assembly, purified cannabinoid from cannabis, isolated terpene, ethanol, and a hydrofluorocarbon propellant.

\* \* \* \* \*

(12) EX PARTE REEXAMINATION CERTIFICATE (11848th)
United States Patent
Nguyen

(10) Number: US 10,231,948 C1
(45) Certificate Issued: May 18, 2021

(54) METERED DOSE INHALER COMPOSITIONS, SYSTEMS, AND METHODS

(71) Applicant: Jason Ty Nguyen, Phoenix, AZ (US)

(72) Inventor: Jason Ty Nguyen, Phoenix, AZ (US)

(73) Assignee: VAPEN, LLC, Phoenix, AZ (US)

Reexamination Request:
No. 90/014,498, Apr. 17, 2020

Reexamination Certificate for:
Patent No.: 10,231,948
Issued: Mar. 19, 2019
Appl. No.: 15/905,662
Filed: Feb. 26, 2018

Related U.S. Application Data

(60) Provisional application No. 62/463,925, filed on Feb. 27, 2017.

(51) Int. Cl.
| | | |
|---|---|---|
| *A61K 36/185* | (2006.01) | |
| *A61K 47/06* | (2006.01) | |
| *A61K 47/10* | (2017.01) | |
| *A61K 47/14* | (2017.01) | |
| *A61M 15/00* | (2006.01) | |
| *A61K 31/352* | (2006.01) | |
| *A61K 9/00* | (2006.01) | |
| *A61K 9/12* | (2006.01) | |

(52) U.S. Cl.
CPC ............ *A61K 31/352* (2013.01); *A61K 9/008* (2013.01); *A61K 9/124* (2013.01); *A61K 36/185* (2013.01); *A61K 47/06* (2013.01); *A61K 47/10* (2013.01); *A61K 47/14* (2013.01); *A61M 15/009* (2013.01); *A61M 15/0068* (2014.02); *A61M 2205/12* (2013.01)

(58) Field of Classification Search
CPC ........ A61K 9/008; A61K 31/352; A61K 7/06; A61K 47/10; A61K 9/124; A61K 36/185; A61K 47/14; A61M 15/009
See application file for complete search history.

(56) References Cited

To view the complete listing of prior art documents cited during the proceeding for Reexamination Control Number 90/014,498, please refer to the USPTO's public Patent Application Information Retrieval (PAIR) system under the Display References tab.

*Primary Examiner* — Carlos N Lopez

(57) ABSTRACT

Compositions, systems, and methods that can be used with a pressurized metered dose inhaler are disclosed. A pharmaceutical composition for use in a pressurized metered dose inhaler can comprise a cannabinoid composition, a co-solvent, a terpene composition, and a propellant. A pharmaceutical composition may be soluble. A system can comprise a plurality of cannabinoid compositions and/or a plurality of terpene compositions available in various combinations. One of a plurality of cannabinoid compositions and terpene composition combinations may be user-selectable in response to various factors such as a desired therapeutic benefit, sedative effect, flavor profile, or a combination of the foregoing. A method of formulating a soluble pMDI pharmaceutical composition comprising a cannabinoid composition, a co-solvent, a terpene composition, and a propellant is disclosed.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

New claims 2-6 are added and determined to be patentable.

1. An inhaler system consisting essentially of an actuator, a user interchangeable canister assembly, *14 to 20% w/w* purified cannabinoid from cannabis, *0.5 to 4.0% w/w* isolated terpene, *14% to 20% w/w* ethanol, and *55% to 72% w/w of* a hydrofluorocarbon propellant.

2. *The inhaler system of claim 1, wherein the purified cannabinoid from cannabis is selected from the group consisting of delta-9-tetrahydrocannabinol (THC), tetrahydrocannabinolic acid (THCA), delta-8-tetrahydrocannabinol (D8THC), cannabidiol (CBD), cannabidiolic acid (CBDA), cannabinol (CBN), cannabinolic acid (CBNA), tetrahydrocannabinovarin (THCV), tetrahydrocannabinovarinic acid (THCVA), cannabidivarin (CBDV), cannabidivarin acid (CBDVA), cannabigerol (CBG), cannabigerolic acid (CBGA), cannabichromene (CBC), cannabichromenic acid (CBCA), cannabinodiol (CBND), and cannabinodiolic acid (CBNDA).*

3. *The inhaler system of claim 1, wherein the isolated terpene comprises one of myrcene, linalool, and d-limonene.*

4. *The inhaler system of claim 1, wherein a user interchangeable canister assembly is selected in response to a combined flavor preference and sedation preference.*

5. *The inhaler system of claim 1, wherein the isolated terpene comprises at least about 0.5%, or at least about 0.75%, or at least about 1.0%, or at least about 1.25%, or at least about 1.5%, or at least about 1.75%, or at least about 2.0%, or at least about 3.0%, or at least about 4.0% by weight (w/w).*

6. *The inhaler system of claim 1, wherein the isolated terpene is selected from the group consisting of α-pinene, camphene, α-pinene, β-pinene, β-myrcene, δ-3-carene, d-limonene, α-terpinene, p-cymene, eucalyptol, ocimene, γ-terpinene, terpinolene, linalool, (−)-isopulegol, geraniol, β-caryophyllene, α-humulene, nerolidol, (−)-guaiol, (−)-α-bisabolol, (−)-caryophylene oxide, α-phellandrene, fenchol, borneol, terpineol, sabinene, camphor, isoborneol, α-cedrene, phytol, valencene, pulegone geranyl acetate, and menthol.*

\* \* \* \* \*